United States Patent

Hill et al.

[11] Patent Number: 6,014,652
[45] Date of Patent: *Jan. 11, 2000

[54] OBJECT CLASSIFICATION AND IDENTIFICATION SYSTEM

[75] Inventors: Wayne S. Hill, Westborough, Mass.; Frank J. Heirtzler, Londonderry, N.H.

[73] Assignee: Foster-Miller, Inc., Waltham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/736,441

[22] Filed: Oct. 24, 1996

Related U.S. Application Data

[63] Continuation-in-part of application No. 08/333,213, Nov. 2, 1994, Pat. No. 5,600,073.

[51] Int. Cl.[7] .................................................. G06F 15/18
[52] U.S. Cl. ................................. 706/16; 706/15; 706/17
[58] Field of Search .................................... 356/238, 383, 356/375; 364/513; 382/14, 15; 395/21, 22; 706/15–17

[56] References Cited

U.S. PATENT DOCUMENTS

| 4,555,953 | 12/1985 | Dario et al. | 73/862.046 |
| 5,138,216 | 8/1992 | Woodruff et al. | 310/316 |
| 5,247,584 | 9/1993 | Krogmann | 382/14 |
| 5,319,443 | 6/1994 | Watanabe et al. | 356/375 |
| 5,485,908 | 1/1996 | Wang et al. | 194/317 |

OTHER PUBLICATIONS

Sage et al. "Estimation Theory with Applications to Communications and Control," McGraw–Hill, Inc, Dec. 31, 1971.

*Primary Examiner*—Tariq R. Hafiz
*Assistant Examiner*—Wilbert L. Starks
*Attorney, Agent, or Firm*—Iandiorio & Teska; Brian J. Colandreo

[57] ABSTRACT

An object classification and identification system including stored discriminator quantities indicative of the surface characteristics of known objects; an arm coupled to a detector which provides a voltage signal which varies relative to the surface characteristics of a detected object as the arm moves over the detected object; a computer programmed to calculate a plurality of discriminator quantities indicative of the surface characteristics of the detected object based on the voltage signal; and a neural network used for matching the calculated discriminator quantities of the detected object with the stored discriminator quantities indicative of the surface characteristics of known object.

22 Claims, 5 Drawing Sheets

OBJECT CLASSIFICATION AND IDENTIFICATION SYSTEM

RELATED APPLICATIONS

This is a continuation-in-part of U.S. patent application Ser. No. 08/333,213, filed Nov. 2, 1994, now U.S. Pat. No. 5,600,073.

FIELD OF INVENTION

This invention relates to a system which can broadly or narrowly classify an object or even identify an object.

BACKGROUND OF INVENTION

Artificial intelligence has been hampered to some extent because some human senses are difficult to synthesize. Computers do not see too well and robots have difficulty with a sense humans take for granted: touch. Even without sight, it is relatively simple for humans, through touch, to tell the difference between a rock, a desk, a pipe—even the difference between a metal and a plastic pipe. Computers and robots and other forms of artificial intelligence do not have this capability.

The need for an artificial intelligence system which can "feel" and classify and even identify objects is self evident: if robots can be made to select or avoid the proper object out of a group of objects, the tedious task of sorting different objects by hand could be automated, and objects could be remotely detected and classified as either harmless or dangerous before human contact is made.

Unfortunately, no artificial intelligence based system exists which automatically classifies or identifies objects on the basis of touch.

SUMMARY OF INVENTION

It is therefore an object of this invention to provide an object classification system.

It is a further object of this invention to provide such an object classification system which identifies objects on the basis of touch.

It is a further object of this invention to provide such an object classification system which, depending on the implementation, can be made to broadly classify objects (e.g. man-made or naturally occurring), more narrowly classify objects (e.g. plastic or wood), or can even be made to identify an object (e.g. pipe, brick, rock).

It is a further object of this invention to provide such an object classification system which classifies or identifies an object by analyzing the surface characteristics of the object.

It is a further object of this invention to provide such an object classification system which advances the state of the art in artificial intelligence by adding the sense of touch to artificial intelligence based systems.

This invention results from the realization that objects can be broadly classified (e.g. man-made or naturally occurring), more narrowly classified (e.g. plastic or wood), or even identified (e.g. pipe, brick, rock) by sensing the vibrations generated as an arm with a friction surface moves over the object; extracting, from the vibration signal, a number of "discriminator quantities" indicative of the surface characteristics of the object; and then applying these discriminator quantities to a neural network trained to recognize, classify, and even identify objects based on their unique discriminator quantities. In other embodiments, any sensor capable of producing a signal which varies in response to surface characteristics can be used in accordance with this invention.

This invention features and may suitably comprise, include, consist essentially of, or consist of an object classification system. There are means for storing discriminator quantities indicative of the surface characteristics of previously classified objects, a sensor which provides a signal which varies relative to the surface characteristics of a detected object as the sensor moves with respect to the detected object, calculating means, responsive to the varying signal from the sensor, for calculating a plurality of discriminator quantities indicative of the surface characteristics of the detected object; and means for matching the calculated discriminator quantities with the stored discriminator quantities for classifying the detected object.

The means for storing preferably includes a neural network trained in accordance with the discriminator quantities indicative of the surface characteristics of previously classified objects. The means for matching includes means for applying the trained neural network to the calculated discriminator quantities.

The sensor may include an arm and means (such as piezoelectric detector) for detecting movement of the arm as the arm moves over the surface of a detected object. Other sensors which contact the surface and sensors which do not contact the surface of the object may be used provided the sensor provides a signal which varies in some way in response to the surface of the object. Further included are means for automatically moving the arm with respect to the surface of the detected object. Also, the arm may include a friction surface for amplifying the signal. There are a number of discriminator quantities calculated on a computer in this invention to make sense out of the signal generated as the arm moves over the surface of an object: the calculating means includes means for determining the mean of the varying signal and the number of excursions above one standard deviation from the mean—a discriminator quantity indicative of surface roughness of a detected object. The calculating means may include means for determining the pulse width of the varying signal between upwards and downward crossings of the varying signal with respect to one standard deviation of the mean—a discriminator quantity indicative of the size of bumps on the surface of a detected object. The calculating means may include means for determining the length of the varying signal for each excursion above one standard deviation of the mean—a discriminator quantity indicative of the texture of bumps on the surface of a detected object. The calculating means may include means for determining the time between one excursion above one standard deviation of the means and the next excursion above one standard deviation of the mean—a discriminator quantity indicative of the distance between bumps on the surface of a detected object. The calculating means may include means for determining the time between one excursion below one standard deviation of the mean and the next excursion below one standard deviation of the mean—a discriminator quantity indicative of the distance between bumps on the surface of a detected object. The calculating means may include means for determining the number of excursions above or below one standard deviation from the mean—a discriminator quantity indicative of the roughness of the surface of a detected object. The calculating means may include means for determining the RMS value of the varying signal—a discriminator quantity indicative of a measure of large scale roughness of the surface of a detected object. The calculating means may include means for determining the time between the end of an upward excursion above one standard deviation of the mean—discriminator quantity indicative of bumps and depressions on the surface of a detected object. The calculating may also include means for performing an FFT calculation of the varying signal and means for determining the mean value of the amplitude calculation for a number of preestablished frequency ranges—a discriminator quantity indicative of a measure of the elasticity of the detected object. The calculating means may include means for calculating a plurality of discriminator quantities for a number of samples of the varying signal as the sensor moves over the surface of the detected object and further includes means for determining the average change in the varying signal between samples—a discriminator quantity indicative of the surface roughness of the detected object. Also, the calculating means may include means for determining the length of the varying signal for a number of samples as a discriminator quantity indicate of the overall texture of the surface of the detected object. Finally, the calculating means may include means for determining the characteristic autocorrelation time of the varying signal—a discriminator quantity indicative of the uniformity of the surface of a detected object.

This invention further features a method of automatically classifying an object comprising: storing a plurality of discriminator quantities indicative of the surface characteristics of previously classified objects, moving a sensor over the surface of an object to be classified and providing a signal which varies relative to the surface characteristics of the object, calculating a plurality of discriminator quantities based on said varying signal and indicative of the surface characteristics of the detected object, and matching the calculated discriminator quantities with the stored discriminator quantities for classifying the detected object.

An object classification and identification system according to this invention features means for storing discriminator quantities indicative of the surface characteristics of known objects, a sensor which provides a signal which varies relative to the surface characteristics of an unknown object as the sensor moves with respect to the surface of the unknown object, calculating means, responsive to the varying signal from the sensor, for calculating a plurality of discriminator quantities indicative of the surface characteristics of the unknown object, and means for matching the calculated discriminator quantities of the unknown object with the stored discriminator quantities of known objects.

The invention also features a neural network trained in accordance with discriminator quantities indicative of the surface characteristics of previously classified objects, a sensor which provides a signal which varies relative to the surface characteristics of an unknown object as the sensor moves with respect to the surface of the unknown object, calculating means, responsive to the varying signal from the sensor, for calculating a plurality of discriminator quantities indicative of the surface characteristics of the unknown object, and means for classifying the detected object including means for applying the trained neural network to the calculated discriminator quantities.

A number of discriminator quantities are calculated: a discriminator quantity indicative of the size of bumps on the surface of a detected object, a discriminator quantity indicative of the texture of bumps on the surface of a detected object, a discriminator quantity indicative of the distance between bumps on the surface of a detected object, a discriminator quantity indicative of bumps and depressions on the surface of a detected object, and/or a discriminator quantity indicative of a measure of the elasticity of the detected object.

DESCRIPTION OF DRAWINGS

Other objects, features and advantages will occur to those skilled in the art from the following description of a preferred embodiment and the accompanying drawings, in which.

DISCLOSURE OF PREFERRED EMBODIMENTS

Figure 1:
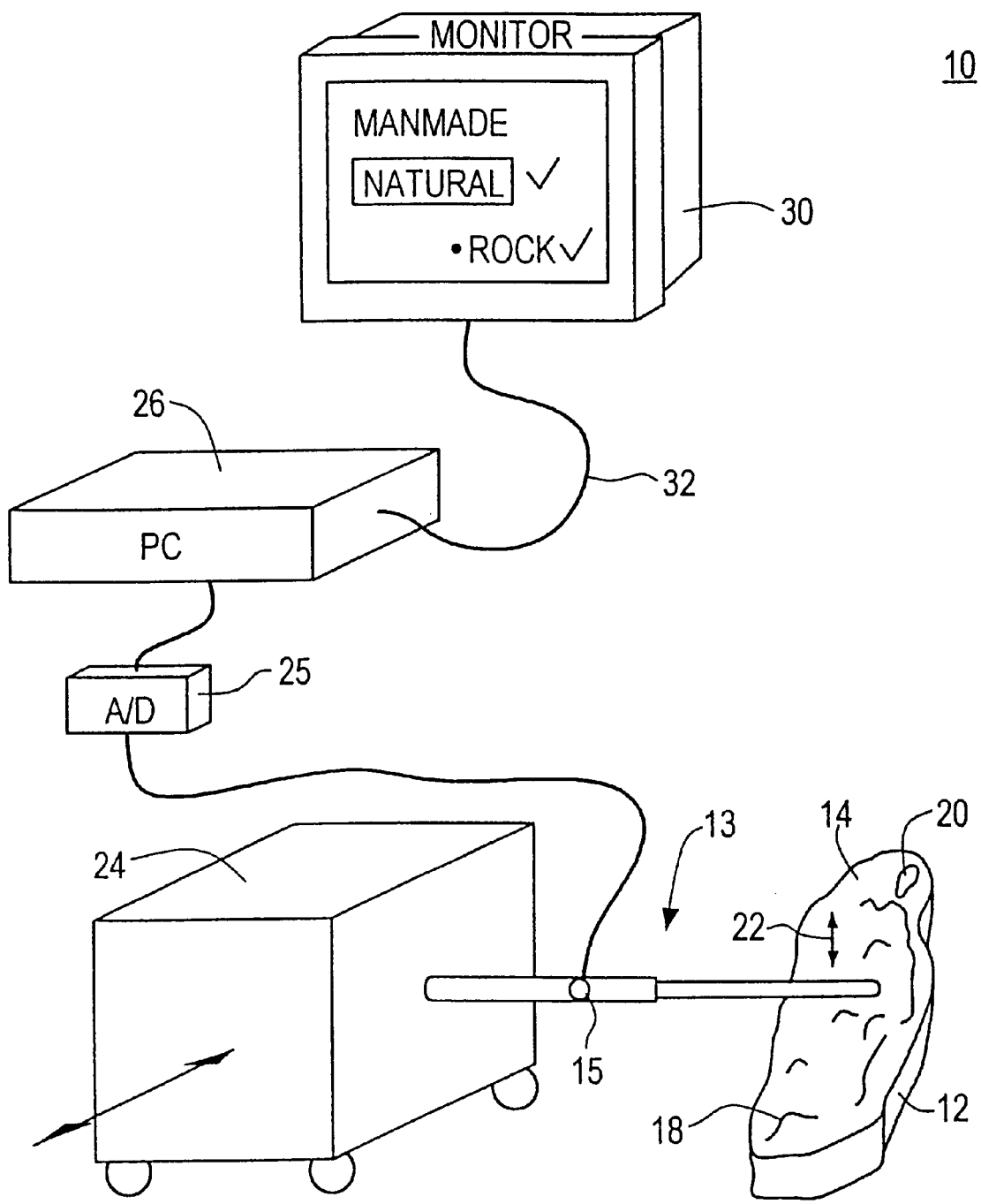
FIG. 1 is a schematic diagram of the object classification system of this invention.

Depending on the performance requirements and the design parameters of the specific implementation, object classification system 10, FIG. 1 broadly classifies (e.g. man-made or naturally occurring), narrowly classifies (e.g. plastic or wood) and/or identifies (e.g. pipe, rock, brick) object 12. Also, system 10 could be implemented to analyze only the surface characteristics of surface 14 (e.g. roughness, etc). Other possible uses of system 10 will be understood by those skilled in the art.

System 10, in a preferred embodiment, includes sensor 13 attached to some means 24 (e.g. a robot or motorized radio controlled vehicle) for moving sensor 13 over surface 14 of object 12. Sensor 13 includes arm 16 having a friction surface which contacts surface 14 of object 12. In the prototype, arm 16 was a carbide grit edge rod saw available from Rule Industries, Burlington, Mass. Sensor 13 also includes piezoelectric detector 15 coupled to arm 16. Arm 16 is biased in a static position and, as it moves over surface 14 of object 12, bumps 18 and depressions 20 on surface 14 of object 12 cause arm 16 to vibrate in the direction shown by arrow 22. These vibrations are sensed by piezoelectric detector 15 resulting in the varying voltage signal shown in FIG. 4 discussed infra. This signal is ultimately used to identify object 12. A/D converter 25 converts the voltage signal from piezoelectric detector 15 into a digital signal and the "Labview" computer program is used to convert this signal into the data analyzed by computer 26.

Figure 6:
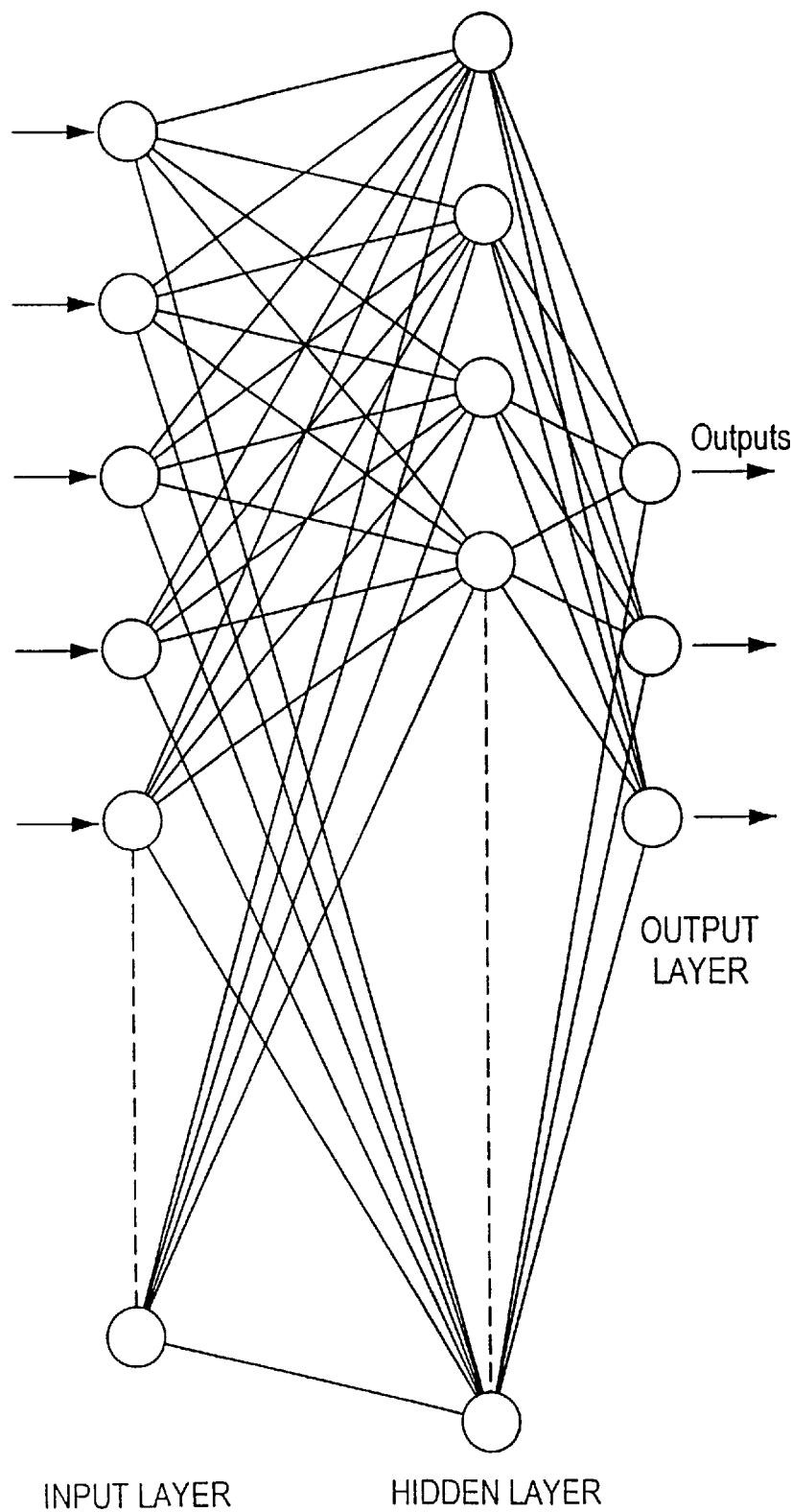
FIG. 6 is a schematic diagram of a neural network trained in accordance with this invention to recognize, classify, and identify objects based on their unique discriminator quantities.

Computer 26 includes a calculation routine which takes as input over line 28 the varying voltage signal produced by piezoelectric detector 15 as arm 16 traverses surface 14 of object 12. As explained in more detailed below, the calculation routine calculates a number of "discriminator quantities" indicative of the surface characteristics of the detected object 12 based on the varying voltage signal produced as arm 16 moves over surface 14. Computer 26 also includes stored discriminator quantities indicative of the surface characteristics (e.g., roughness, smoothness, bump texture, size of bumps and distance between bumps, etc.) of previously classified (e.g. manmade or naturally occurring) and/or identified objects (e.g. plastic pipes, metal pipes, rocks, bricks). Computer 26 typically includes a neural network as shown in FIG. 6 trained in accordance with the discriminator quantities indicative of the surface characteristics of previously classified or identified objects.

Computer 26 matches the calculated discriminator quantities of the unknown object with the stored discriminator quantities of previously classified objects in order to classify or identify the detected object. This is typically accomplished by applying the trained neural network to the calculated discriminator quantities. Once a match is made, the result is displayed on monitor 30 connected to computer 26 by line 32.

Alternatively, the result of the match and the information which classifies or identifies object 14 can be used in artificial intelligence based systems to perform a number of different tasks: robots can be made to select or avoid the proper object out of a group of objects, objects can be sorted by class, and/or objects can be remotely detected and classified as either harmless or dangerous before human contact is made.

Figure 2:
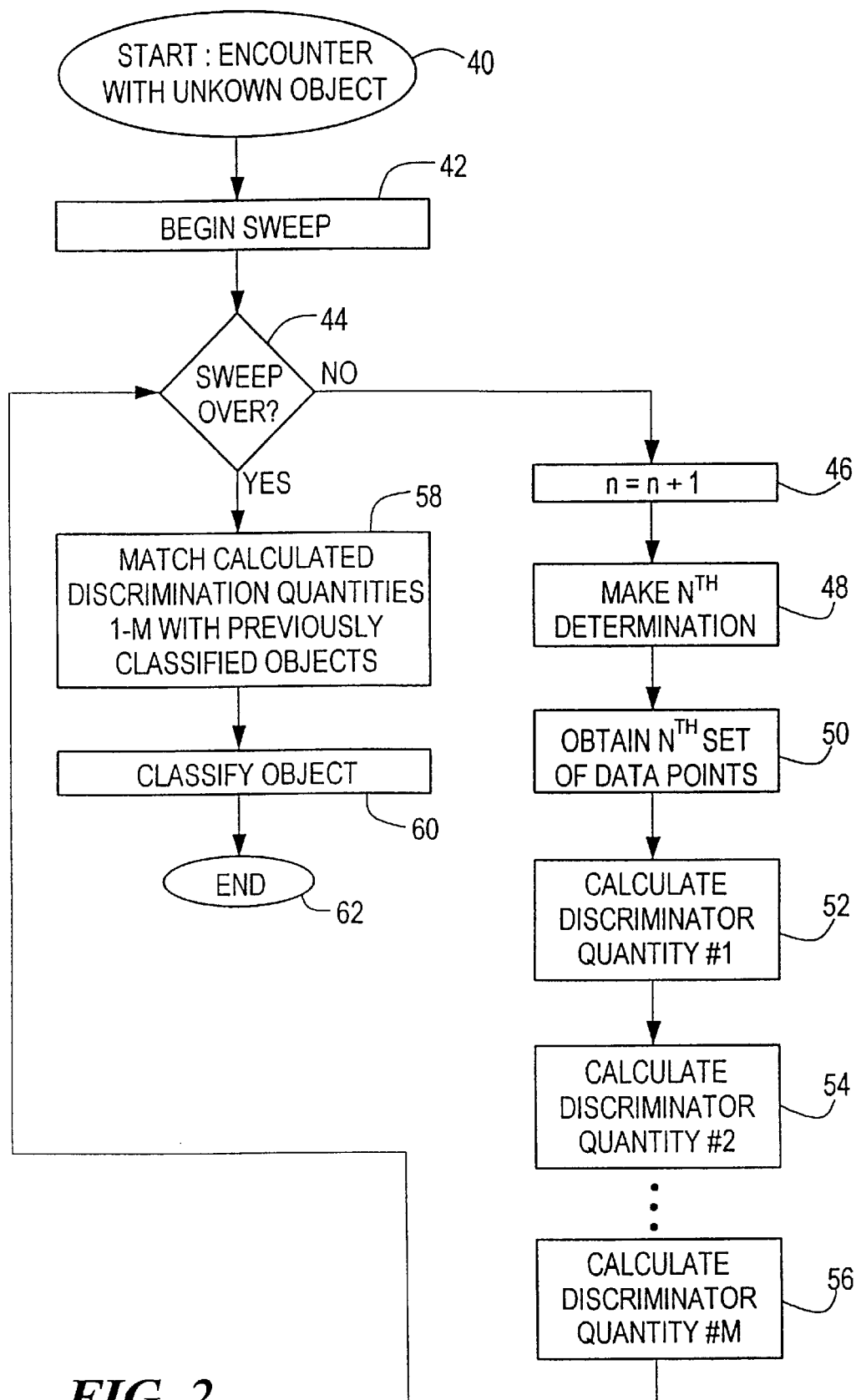
FIG. 2 is a flow chart depicting the method of operation of the object classification system shown in FIG. 1.

The method of operation of object classification system 10, FIG. 1 is shown in FIG. 2. When arm 16 FIG. 1 first encounters object 12, (step 40, FIG. 2), arm 16 is caused by means 24 to sweep over surface 14 of object 12 (step 42, FIG. 2). During the sweep, step 44, a number of determinations are made, steps 46 and 48. During each determination, a number of data points are obtained, step 50, from the signal generated by piezoelectric detector 15, FIG. 1 as arm 16 vibrates up and down in the direction shown by arrow 22 due to irregularities on the surface 14 of object 12. For each data set, a number of discriminator quantities are calculated, steps 52, 54 and 56, FIG. 2. Examples of these discriminator quantities are explained below with reference to FIG. 4.

If arm 16, FIG. 1 has not yet traversed the entire surface 14 of object 12 as shown in step 44, FIG. 2, another determination is made, steps 46 and 48 and another set of data points are accumulated, step 50. This process continues in a like manner until arm 16 FIG. 1 has fully traversed surface 14 of object 12.

The calculation routine of computer 26, FIG. 1 now has a number of different calculated discriminator quantities for a number of samples of data points. These calculated discriminator quantities are then matched, step 58, FIG. 2 with discriminator quantities of previously classified objects stored on computer 26, FIG. 1. As discussed above, computer 26 includes a neural network trained in accordance with the discriminator quantities indicative of the surface characteristics of previously classified or identified objects. In step 50, FIG. 2, this trained neural network is applied to the calculated discriminator quantities indicative of the surface characteristics of a detected object and the neural network classifies the object, step 60. Object 12, FIG. 1 has now been classified and the procedure stops, steps 62, FIG. 2 until another unknown object is to be classified or identified.

Figure 3:
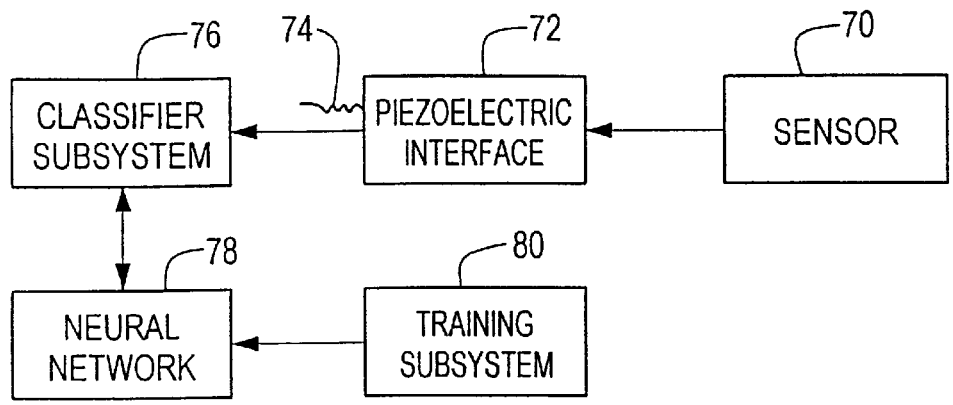
FIG. 3 is a block diagram of the major subsystem components of the object classification system shown in FIG. 1.

In a preferred embodiment, object classification 10, FIG. 1 includes five major subsystems as shown in FIG. 3. Sensor 70 and signal interface 72 provides time varying voltage signal 74 to classifier a subsystem 76. Neural network 78 is trained in accordance with a training subsystem 80 and applied to the data of classifier subsystem 76 in order to classify or identify an unknown object. Sensor 70 includes arm 16, FIG. 1 connected to a detector 15 to provide time varying voltage signal 74, FIG. 3, to classifier subsystem 76. Neural network 78 resides on computer 26, FIG. 1 and is currently manually trained by moving arm 16, over the surface of known objects (e.g. pipes, rocks, bricks, pieces of wood) in order to train the neural network. Classifier subsystem 76, FIG. 3 includes a number of software routines operating on computer 26, FIG. 1 which both calculate the discriminator quantities from signal 74, FIG. 3 for an unknown object and then also applies those calculated discriminator quantities to trained neural network 78.

Figure 4:
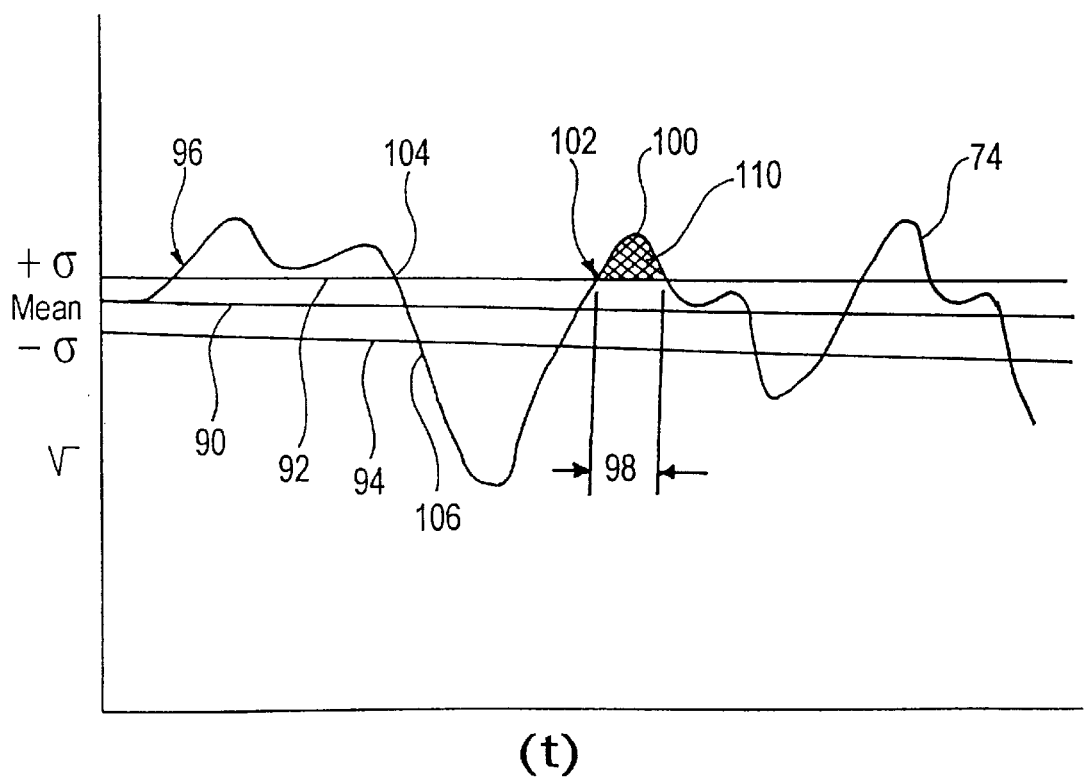
FIG. 4 is a graph of a typical vibration wave form signal relating to the surface characteristics of a detected object analyzed by the object classification system of this invention.

Signal 74, FIG. 4, generated by piezoelectric detector 15, FIG. 1 as arm 16 traverses the surface 14 of object 12 is used in this invention in order to classify or identify unknown object 12. A number of discriminator quantities are calculated from signal 74.

The mean 90 of signal 74, is calculated as is one standard deviation 92 above and one standard deviation 94 below mean 90 since these data points are used in the calculation of various discriminator quantities. One calculated discriminator quantity is the number of excursions per sample above one standard deviation 92 from the mean 90 as shown for excursion 96. This discriminator quantity is indicative of the surface roughness of a detected object. A routine operating on computer 26, FIG. 1 calculates this discriminator quantity and the other discriminator quantities of the invention.

One encounter or sweep of arm 16 over surface 14 of object 12, FIG. 1 may include several (e.g. 7–8) determinations where N (e.g. 1,248) data points are collected during each determination. The calculations performed in order to accumulate the discriminator quantities are performed on each N set of data points. Therefore, for example, for an encounter time of one second, there may be as many as 10,000 samples. And, the discriminator quantity indicative of surface roughness as delineated above may be calculated and recalculated a number of times, once for each determination.

Another discriminator quantity, indicative of the size of bumps on the surface of the detected object, is the pulse width 98 between upwards and downwards crossings of the varying signal 74 with respect to one standard deviation of the mean. The actual length of signal 74 (i.e. sum of absolute value of changes in the reading) between upwards and downwards crossings with respect to one standard deviation of the mean as shown at 100 is another discriminator quantity indicative of the texture of bumps on the surface of the detected object. The time from the beginning of one upward excursion as shown in 96 to the next upward excursion as shown at 102 above (or alternatively below) one standard deviation from the means is a discriminator quantity indicative of the distance between bumps on the surface of a detected object. The discriminator quantity representative of the number of excursions above or below one standard deviation from the mean is indicative of the roughness of the surface of the detected object. Still another discriminator quantity is RMS value of signal 74 which is indicative of the large scale roughness of the surface of the detected object. The time between the end of upper excursion 96 as shown as 104 and the beginning of a downward excursion as shown at 106 is a discriminator quantity indicative of bumps and depressions on the surface of a detected object.

The calculation routines operating on computer 26, FIG. 1 according to the flow chart shown in FIG. 2 perform an FFT calculation of varying signal 74, FIG. 4 and then determine the mean value of the amplitude for a number of preestablished frequency ranges. This discriminator quantity is indicative of a measure of the elasticity of the object. The mean value of the amplitude for frequencies between 50 hertz to 200 hertz, between 200 to 400 hertz, and between 500 to 900 hertz was found to accurately classify objects according to their elasticity. The average change in varying signal 74 between samples is a discriminator quantity indicative of the surface roughness of the detected object. The length of signal 74 for a number of samples is a discriminator quantity indicative of the overall texture of the surface of the object to be classified. The average area of each excursion above one standard deviation from the mean as shown at 110 for excursion 102 is indicative of the size of the bumps on the surface of the object.

Another discriminator quantity that can be used to characterize the surface is the characteristic autocorrelation time. The autocorrelation function is calculated by time-shifting one copy of a data set by a "time lag" and summing the product of corresponding values:

$$C_{xx}(j) = \frac{1}{n-j}\sum_{i=1}^{n-j}[X_i(X_{i+J})] \quad (1)$$

Figure 5:
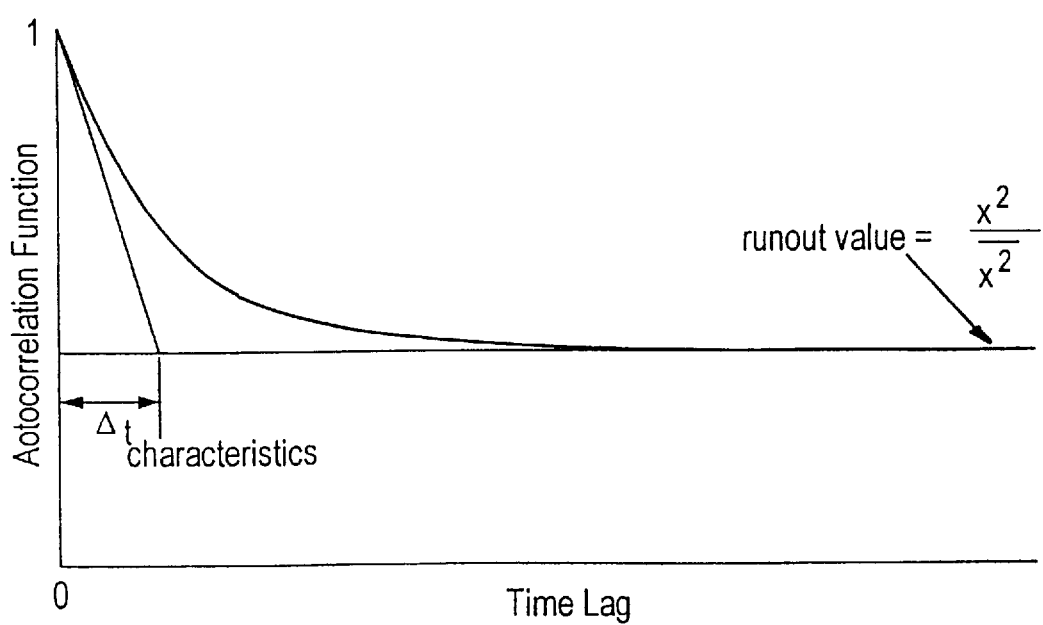
FIG. 5 is a graph of the autocorrelation function used in accordance with this invention.

This function is often normalized so that the value for a zero time lag (j=O) is unity. A typical autocorrelation function for chaotic data is illustrated in FIG. 5. The value for zero time lag (before normalization) is $$C_{xx}(0) = \frac{1}{n}\sum_n X_i^2 = \overline{X^2} \quad (2)$$

The uncorrelated "runout" behavior is $$C_{xx}(\infty) = \left[\frac{1}{n}\sum_n X_i\right]^2 = \overline{X}^2 \quad (3)$$

The characteristic autocorrelation time is the initial rate at which the autocorrelation of the data set leaves the initial point and approaches the "runout" behavior. The characteristic autocorrelation time reflects the time scale over which variations in the signal are linearly unrelated. For surfaces, this reflects the length scale of surface roughness. For many time series data, $\Delta t_{characteristic} \gg \Delta t$ sample, so it can be easily approximated by $$\Delta t_{characteristic} = n\Delta t_{sample}\frac{\overline{X^2} - C_{xx}(n\Delta t_{sample})}{\overline{X^2} - \overline{X}^2} \quad (4)$$

where $\Delta t_{sample}$ is the data sampling interval and n the number of samples by which one copy of the signal is "slipped" to calculate the initial slope. In many cases, it is sufficient to use n=1 resulting in a simple, easily implemented calculation algorithm. While the result obtained varies with n and sampling time, the results obtained with a given set of calculating parameters vary consistently with surface conditions. Thus, it is more important to consistently apply a single calculation algorithm than to use the most accurate algorithm.

Once an appropriate set of discriminator quantities has been determined for a surface, a neural network, FIG. 6, can be used to classify or identify the surface according to surfaces that were previously tested. This approach combines confidence in the discriminator quantities with a fast, fault tolerant, nonlinear correlation achievable with a small neural network. The neural network used in the initial reduction to practice is based on a commercially available neural network simulation program "NeuroShell 2", available from Ward Systems Group of Frederick, Md.

To test this approach, the data graphs in FIG. 4 calculate the discriminator quantities described above and these were used to train the neural network shown in FIG. 6 to classify the object according to preset categories. The neural network was configured as a conventional back-propagation network with 16 input nodes corresponding to the 16 discriminator quantities. Twenty hidden nodes were fully interconnected with these input nodes and also with one output node corresponding to object classification. Back-propagation training was used with various learning rates and momentum values to optimize network performance. To avoid overtraining, network 100 was trained using data from only 50% of the test conditions. A new network configuration was saved only if it improved the prediction of the classification for the other half of the test conditions. The results of this analysis for a series of test objects including metallic and non-metallic, rough and smooth objects of various sizes and shapes, show an extremely good correlation between the actual and predicted object classifications for all tests conditions. In fact, out of a test series of 235 data sets, this procedure accurately predicted 210 of them, better than 89% accuracy overall.

Note, however, that other discriminator quantities may be calculated and computer 26 programmed accordingly in order to automatically perform the calculations. Also, computer 26 which operates the software for calculating the discriminator quantities and the trained neural network and the other subsystems shown in FIG. 1 may reside in one package and computer 26 could be programmed to operate robot means 24 to perform the appropriate task with respect to object 14 once it is classified. Therefore, specific features of the invention are shown in some drawings and not others, this is for convenience only as some feature may be combined with any or all of the other features in accordance with the invention.

Other embodiments will occur to those skilled in the art and are within the following claims:

What is claimed is:

1. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the mean of the varying signal and the number of excursions above one standard deviation from the mean; and means for matching the calculated discriminator quantities with the stored discriminator quantities for classifying the detected object.

2. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the mean of the varying signal and the pulse width of the varying signal between upwards and downwards crossings of the varying signal with respect to one standard deviation above the mean; and means for matching the calculated discriminator quantities with the stored discriminator quantities for classifying the detected object.

3. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the mean of the varying signal and the length of the varying signal for each excursion above one standard deviation above the mean; and means for matching the calculated discriminator quantities with the stored discriminator quantities for classifying the detected object.

4. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the time period between one excursion above one standard deviation of the mean of the varying signal and the next excursion above one standard deviation above the mean; and means for matching the calculated discriminator quantities with the stored discriminator quantities for classifying the detected object.

5. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the time period between one excursion below one standard deviation of the mean of the varying signal and the next excursion below one standard deviation above the mean; and means for matching the calculated discriminator quantities with the stored discriminator quantities for classifying the detected object.

6. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the number of excursions above or below one standard deviation from the mean of the varying signal; and means for matching the calculated discriminator quantities with the stored discriminator quantities for classifying the detected object.

7. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the RMS value of the varying signal; and means for matching the calculated discriminator quantities with the stored discriminator quantities for classifying the detected object.

8. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the time period between the end of an upward excursion above one standard deviation above the mean of the varying signal and the beginning of a downward excursion below one standard deviation above the mean; and means for matching the calculated discriminator quantities with the stored discriminator quantities for classifying the detected object.

9. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including an FFT calculation of the varying signal and the mean amplitude value for a number of preestablished frequency ranges; and means for matching the calculated discriminator quantities with the stored discriminator quantities for classifying the detected object.

10. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object for a number of samples of the varying signal including the average absolute value change in the varying signal between samples; and means for matching the calculated discriminator quantities with the stored discriminator quantities for classifying the detected object.

11. An object classification system comprising:

means for storing discriminator quantities related to certain surface characteristics of previously classified objects;

a sensor which provides a signal which varies relative to surface characteristics of a detected object as said sensor moves with respect to the detected object;

calculating means, responsive to the varying signal from the sensor, for calculating a plurality of discriminator quantities related to surface characteristics of the detected object including the characteristic autocorrelation time of the varying signal; and means for matching the calculated discriminator quantities with the stored discriminator quantities for classifying the detected object.

12. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the mean of the varying signal and the number of excursions above one standard deviation from the mean; and matching the calculated discriminator quantities with the stored discriminator quantities for classifying the detected object.

13. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the mean of the varying signal and the pulse width of the varying signal between upwards and downwards crossings of the varying signal with respect to one standard deviation above the mean; and matching the calculated discriminator quantities with the stored discriminator quantities for classifying the detected object.

14. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the mean of the varying signal and the length of the varying signal for each excursion above one standard deviation above the mean; and matching the calculated discriminator quantities with the stored discriminator quantities for classifying the detected object.

15. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the time period between one excursion above one standard deviation above the mean of the varying signal and the next excursion above one standard deviation of the mean; and matching the calculated discriminator quantities with the stored discriminator quantities for classifying the detected object.

16. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the time period between one excursion below one standard deviation above the mean of the varying signal and the next excursion below one standard deviation above the mean; and matching the calculated discriminator quantities with the stored discriminator quantities for classifying the detected object.

17. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the number of excursions above or below one standard deviation from the mean of the varying signal; and matching the calculated discriminator quantities with the stored discriminator quantities for classifying the detected object.

18. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the RMS value of the varying signal; and matching the calculated discriminator quantities with the stored discriminator quantities for classifying the detected object.

19. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the time period between the end of an upward excursion above one standard deviation of the mean of the varying signal and the beginning of a downward excursion below one standard deviation above the mean; and matching the calculated discriminator quantities with the stored discriminator quantities for classifying the detected object.

20. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including an FFT calculation of the varying signal and the mean amplitude value for a number of preestablished frequency ranges; and matching the calculated discriminator quantities with the stored discriminator quantities for classifying the detected object.

21. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object for a number of samples of the varying signal including the average absolute value change in the varying signal between samples; and matching the calculated discriminator quantities with the stored discriminator quantities for classifying the detected object.

22. An object classification method comprising:

storing discriminator quantities related to certain surface characteristics of previously classified objects;

moving a sensor over a detected object and providing a signal which varies relative to surface characteristics of the detected object as said sensor moves with respect to the detected object;

in response to the varying signal from the sensor, calculating a plurality of discriminator quantities related to surface characteristics of the detected object including the characteristic autocorrelation time of the varying signal; and matching the calculated discriminator quantities with the stored discriminator quantities for classifying the detected object.

* * * * *